(12) United States Patent
Stock et al.

(10) Patent No.: US 7,171,842 B2
(45) Date of Patent: Feb. 6, 2007

(54) BREATH ALCOHOL MEASURING DEVICE

(75) Inventors: Burkhard Stock, Lübeck (DE); Theodor Kater, Lübeck (DE)

(73) Assignee: Dräger Safety AG & Co., KGaA (DE)

( * ) Notice: Subject to any disclaimer, the term of this patent is extended or adjusted under 35 U.S.C. 154(b) by 37 days.

(21) Appl. No.: 11/037,591

(22) Filed: Jan. 18, 2005

(65) Prior Publication Data
US 2005/0223774 A1    Oct. 13, 2005

(30) Foreign Application Priority Data
Apr. 7, 2004  (DE) ...................... 10 2004 017 068

(51) Int. Cl.
*G01N 27/04* (2006.01)
(52) U.S. Cl. ..................................... 73/23.3
(58) Field of Classification Search .................. 73/23.3
See application file for complete search history.

(56) References Cited

U.S. PATENT DOCUMENTS

| 3,886,535 | A | * | 5/1975 | Cirincione ............. 123/143 R |
| 3,950,155 | A | * | 4/1976 | Komiyama .................... 96/111 |
| 3,950,739 | A | * | 4/1976 | Campman .................. 340/628 |
| 4,250,737 | A | * | 2/1981 | Biglin ......................... 73/23.2 |
| 4,770,026 | A |   | 9/1988 | Wolf |
| 5,020,628 | A | * | 6/1991 | Bigliardi et al. ............ 180/272 |
| 6,837,095 | B2 | * | 1/2005 | Sunshine et al. ............ 73/23.2 |
| 2003/0034851 | A1 |   | 2/2003 | Norman et al. |

FOREIGN PATENT DOCUMENTS

| DE | 43 27 312 C2 | 2/1994 |
| WO | WO88/08085 | 10/1988 |
| WO | WO99/47905 | 9/1999 |

OTHER PUBLICATIONS

Liberali, Valentino et al., "Sigma-Delta Processing in Multisensor Systems for Carbon Monoxide Detection" 1996, IEEE publications, available at http://ieeexplore.ieee.org/iel3/ 3834/11198/00541980.pdf?arnumber=541980.*

* cited by examiner

*Primary Examiner*—Michael Cygan
(74) *Attorney, Agent, or Firm*—McGlew & Tuttle, PC

(57) ABSTRACT

A breath alcohol measuring device is provided with a pressure sensor (2) for detecting a signal representative of the breathing air flow and with an electrochemical sensor (1) for detecting a signal representative of the alcohol content in the breathing air and with evaluating means for processing the signals and for determining the breath alcohol concentration. Such a breath alcohol measuring device has a simple design and high measuring accuracy. The pressure sensor (1) and the electrochemical sensor (2) are connected for this purpose with a delta-sigma analog-digital converter (8), which converts the sensor signals directly into digital measured values for determining the alcohol concentration. The pre-amplifiers needed hitherto become unnecessary as a result, which has a number of advantages.

19 Claims, 1 Drawing Sheet

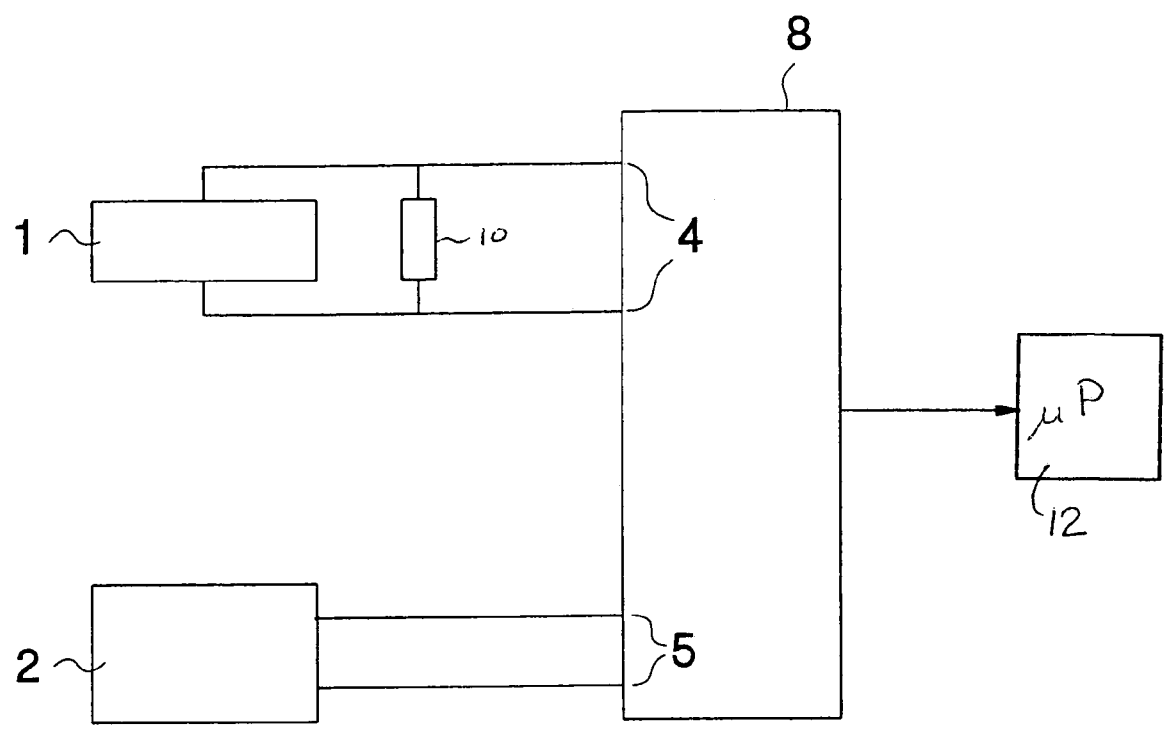

BREATH ALCOHOL MEASURING DEVICE

CROSS REFERENCE TO RELATED APPLICATIONS

This application claims the benefit of priority under 35 U.S.C. § 119 of German Application 10 2004 017 068.1 filed Apr. 7, 2004, the entire contents of which are incorporated herein by reference.

FIELD OF THE INVENTION

The present invention pertains to a breath alcohol measuring device with a pressure sensor for detecting a signal representative of the breathing air flow and with an electrochemical sensor for detecting a signal representative of the breath alcohol content of a breathing air sample and with evaluating means for processing the signals and for determining the breath alcohol concentration.

BACKGROUND OF THE INVENTION

Such breath alcohol measuring devices are known, for example, from DE 43 273 312 C2 and U.S. Pat. No. 4,770,026. The pressure sensor is needed to generate a signal representative of the tidal volume flow. This is needed, on the one hand, to make it possible to monitor the interruption-free expiration by the test subject. Furthermore, the tidal volume flow signal is integrated in order for a preset minimum tidal volume to be able to be determined, which is needed for a reliable measuring result, because a sufficient percentage of breathing air is needed from the depth of the lungs to make it possible to infer the blood alcohol concentration from the breath alcohol concentration.

The electrochemical sensor is exposed to a preset tidal volume sample. Ethanol is selectively reacted at the electrodes of the electrochemical sensor, while an electric current is generated, which subsides slowly, following a rapid rise, which corresponds to the subsiding reaction. The sensor current is integrated over a preset period of time, and the corresponding overall load is estimated from this integrated load value, from which the breath alcohol concentration can be deduced.

In the prior-art breath alcohol measuring devices, the signals of the pressure sensor and of the electrochemical sensor are first amplified in a pre-amplifier or operational amplifier and subsequently sent to an analog-digital converter with a range of 10 bits or 12 bits. The analog processing of the sensor signals prior to their digitization entails various drawbacks.

The electrochemical sensor is connected with a current-voltage converter, which is formed by an operational amplifier fed back to one of its inputs via a resistor. When the supply voltage rises, i.e., when the device is switched on, the operational amplifier passes through non-equilibrium states. As a result, a current is briefly sent to the electrochemical sensor, as a result of which a potential is built up in the sensor. Since it may take about 20 sec until this potential is gradually eliminated again, this leads to a corresponding waiting time until the device becomes ready for use after it had been switched on.

When the device is not switched on, the sensor is not short-circuited, either. Due to thermal effects or gases in the ambient air, a potential may build up, which must first be eliminated after switching on, which in turn leads to a longer waiting time.

Another drawback of the prior-art measuring devices is that a plurality of analog-digital channels with different amplifications are frequently needed to cover the necessary dynamic range, because the evaluating means require a resolution of 7 bits for the integration of the signals of the electrochemical sensor. The ratio of the greatest signal (5 promille at 50° C.) to the lowest signal (0.1 promille at −5° C.) is approx. 1,000/1 (10 bits). The signal of the electrochemical sensor must therefore be distributed in the 10-bit analog-digital converters used typically among a plurality of analog-digital channels with different amplifications in order to cover the dynamic range. This is associated with a number of drawbacks, namely, the need for an increased number of components, increased energy consumption and more complicated signal processing.

Another drawback of the prior-art processing of the analog signals in pre-amplifiers is that electromagnetic radiation may affect the measurements. Electromagnetic radiation causes disturbances in the input circuits of the amplifiers, and these disturbances will be amplified as well and will then cause erroneous measuring results.

The following shall be pointed out in reference to the pressure sensor signal processing. The pressure sensor measures the dynamic pressure generated in the mouthpiece. This dynamic pressure is subsequently converted into a tidal volume flow. Since the lowest detectable tidal volume flow should be approx. 3 L/minute, but the highest approx. 50 L/minute, a very broad dynamic range is obtained here. Furthermore, pressure sensors are designed in the form of a bridge circuit, which already delivers a static offset voltage even without pressure. This static offset voltage limits the possible amplification of the pressure signal to a factor of about 100 in real systems, which will in turn lead to an insufficient digital resolution at low tidal volume flows. Since calibrating systems deliver mostly only a weak current, special mouthpieces will be needed for the calibration. As in the case of the electrochemical sensor, the amplifiers used for the pressure sensor are also susceptible to electromagnetic disturbances.

SUMMARY OF THE INVENTION

The object of the present invention is to provide a breath alcohol measuring device of a simple design, which has a high measuring accuracy.

According to the invention, a breath alcohol measuring device is provided with a pressure sensor for detecting a signal representative of the breathing air flow and with an electrochemical sensor for detecting a signal representative of the alcohol content in the breathing air. An evaluating means is provided for processing the signals and for determining the breath alcohol concentration. The pressure sensor and the electrochemical sensor are connected with a delta-sigma analog-digital converter. The delta-sigma analog-digital converter converts the sensor signals directly into digital measured values for determining the alcohol concentration.

According to the present invention. an analog preprocessing of the signals of the electrochemical sensor and of the pressure sensor can be eliminated. The sensor signals are sent without pre-amplification directly to a delta-sigma analog-digital converter with high resolution. As a result, pre-amplifiers can thus be eliminated altogether. The above-mentioned problems, which arise from the analog pre-amplification, are thus avoided as well.

An individual delta-sigma analog-digital converter with two inputs is used in an advantageous embodiment, and the delta-sigma analog-digital converter is controlled such that it alternatingly processes only the signals of one input and then those of the other input. In an advantageous embodiment, a 24-bit delta-sigma analog-digital converter is used, whose output signals are used by a microprocessor in the evaluating means in order to determine a value for the breath alcohol concentration from the measured signal of the electrochemical sensor and thus to determine an indicator for the blood alcohol concentration.

The present invention will be described below on the basis of an exemplary embodiment shown in the only figure. The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWINGS

The only FIGURE is a block diagram of a part of the breath alcohol measuring device according to the present invention.

DESCRIPTION OF THE PREFERRED EMBODIMENT

Referring to the drawings in particular, the breath alcohol measuring device has an electrochemical sensor 1 and a pressure sensor 2, which are arranged in the known manner in an alcohol test measuring device, such as the measuring device Alcotest 74010 of Dräger Safety AG & Co. KgaA (the Applicant of this application), which is described in Dräigerheft 346 (January-May 1990).

According to the present invention, the difference signals of the electrochemical sensor 1 and the pressure sensor 2 are sent directly, i.e., without pre-amplification, as analog signals to the difference inputs 4 and 5 of the delta-sigma analog-digital converter 8. Such a high-resolution delta-sigma analog-digital converter 8, e.g., such as a 24-bit converter, can evaluate the sensor signals directly in the nV range and send them as digitized data values to the microprocessor 12. The microprocessor or evaluating means will then perform the further calculations and evaluations, namely processing the signals and determining the breath alcohol concentration.

As is shown, the difference lines 6, 7 from the electrochemical sensor 1 are connected by a resistor 10 with low ohmic resistance, so that no disturbing potentials can build up in the electrochemical sensor 1.

The problems inherent to the state of the art, such as lack of dynamics and resolution as well as excessively high susceptibility to electromagnetic disturbances, are completely avoided with the design described. In addition, the breath alcohol measuring device can have a more compact design, because fewer components are present.

While a specific embodiment of the invention has been shown and described in detail to illustrate the application of the principles of the invention, it will be understood that the invention may be embodied otherwise without departing from such principles.

What is claimed is:

1. A breath alcohol measuring device, the device comprising:
    a pressure sensor for detecting a breathing air flow and generating a signal representative of the breathing air flow;
    an electrochemical sensor for detecting an alcohol content in the breathing air and generating an alcohol signal representative of the alcohol content in the breathing air, said alcohol signal having a magnitude in a nV range;
    an evaluating means for processing the signals and for determining the breath alcohol concentration;
    a delta-sigma analog-digital converter, said pressure sensor and said electrochemical sensor being connected with said delta-sigma analog-digital converter, which converts the sensor signals directly into digital measured values for determining the alcohol concentration.

2. A breath alcohol measuring device in accordance with claim 1, wherein said individual delta-sigma analog-digital converter has a first and a second input, wherein said pressure sensor is connected to said first input and said electrochemical sensor is connected to said second input, and signals of said first and second inputs are alternatingly processed by said delta-sigma analog-digital converter.

3. A breath alcohol measuring device in accordance with claim 1, wherein said delta-sigma analog-digital converter is 24-bit delta-sigma analog-digital converter.

4. A breath alcohol measuring device in accordance with claim 1, further comprising:
    a resistor arranged across terminals of said electrochemical sensor for reducing a potential built up in said electrochemical sensor.

5. A breath alcohol measuring device in accordance with claim 4, wherein:
    said electrochemical sensor has difference lines connected to said converter;
    said resistor is connected across said difference lines.

6. A breath alcohol measuring device in accordance with claim 4, wherein:
    said resistor is a low ohmic resistor.

7. A breath alcohol measuring device in accordance with claim 1, wherein:
    at least one of said signals has a ratio between the greatest signal and the lowest signal of approximately 1000/1.

8. A breath alcohol measuring device in accordance with claim 7, wherein:
    said sensor signals are sent directly from said sensors to said delta-sigma analog-digital converter without amplification.

9. A breath alcohol measuring arrangement, the arrangement comprising:
    a pressure sensor for detecting pressure in breathing air flow of a subject and generating a signal representative of the breathing air flow;
    an electrochemical sensor for detecting alcohol content in a breathing air flow of a subject and generating an alcohol signal representative of the alcohol content in the breathing air, a magnitude of said alcohol signal being in a nV range;
    a delta-sigma analog-digital converter, said pressure sensor and said electrochemical sensor being connected with said delta-sigma analog-digital converter, which converts the sensor signals directly into digital measured values.

10. A breath alcohol measuring arrangement in accordance with claim 9, wherein said delta-sigma analog-digital converter is 24-bit delta-sigma analog-digital converter.

11. A breath alcohol measuring arrangement in accordance with claim 9, further comprising:

a resistor arranged across terminals of said electrochemical sensor for reducing a potential built up in said elctochemical sensor.

12. A breath alcohol measuring arrangement in accordance with claim 11, wherein:

said electrochemical sensor has difference lines connected to said converter;

said resistor is connected across said difference lines.

13. A breath alcohol measuring arrangement in accordance with claim 11, wherein:

said resistor is a low ohmic resistor.

14. A breath alcohol measuring arrangement in accordance with claim 9, wherein:

said alcohol signal is sent directly from said sensors to said delta-sigma analog-digital converter without amplification.

15. A breath alcohol measuring arrangement in accordance with claim 14, wherein:

said alcohol signal has a ratio between the greatest signal and the lowest signal of approximately 1000/1.

16. A method of measuring breath alcohol, the method comprising:

using a pressure sensor to measure breathing air flow of a subject and to generate a signal representative of the breathing air flow of a subject;

using an electrochemical sensor to measure breathing air flow of a subject and to generate a signal representative of the alcohol content in the breathing air, a magnitude of said sensor signals being in a nV range; and connecting a delta-sigma analog-digital converter to said pressure sensor and said electrochemical sensor; and using said delta-sigma analog-digital converter to convert the sensor signals directly into digital measured values.

17. A breath alcohol measuring method in accordance with claim 16, wherein said individual delta-sigma analog-digital converter has a first and a second input, wherein said pressure sensor is connected to said first input and said electrochemical sensor is connected to said second input, and signals of said first and second inputs are alternatingly processed by said delta-sigma analog-digital converter.

18. A breath alcohol measuring method in accordance with claim 17, wherein said delta-sigma analog-digital converter is 24-bit delta-sigma analog-digital converter.

19. A breath alcohol measuring method in accordance with claim 16, wherein:

said sensor signals are sent directly from said sensors to said delta-sigma analog-digital converter without amplification, and at least of said signals has a ratio between the greatest signal and the lowest signal of approximately 1000/1.

\* \* \* \* \*